(12) United States Patent
Tabuteau

(10) Patent No.: US 10,695,304 B2
(45) Date of Patent: Jun. 30, 2020

(54) DOSAGE FORMS AND METHODS FOR ENANTIOMERICALLY ENRICHED OR PURE BUPROPION

(71) Applicant: AXSOME THERAPEUTICS, INC., New York, NY (US)

(72) Inventor: Herriot Tabuteau, New York, NY (US)

(73) Assignee: AXSOME THERAPEUTICS, INC., New York, NY (US)

( * ) Notice: Subject to any disclaimer, the term of this patent is extended or adjusted under 35 U.S.C. 154(b) by 0 days.

(21) Appl. No.: 16/579,305

(22) Filed: Sep. 23, 2019

(65) Prior Publication Data

US 2020/0093761 A1    Mar. 26, 2020

Related U.S. Application Data

(63) Continuation-in-part of application No. 16/362,434, filed on Mar. 22, 2019.

(60) Provisional application No. 62/734,021, filed on Sep. 20, 2018, provisional application No. 62/810,880, filed on Feb. 26, 2019.

(51) Int. Cl.
*A61K 31/137* (2006.01)
*A61P 25/26* (2006.01)

(52) U.S. Cl.
CPC .................................. *A61K 31/137* (2013.01)

(58) Field of Classification Search
CPC .............................. A61K 31/137; A61P 25/26
See application file for complete search history.

(56) References Cited

U.S. PATENT DOCUMENTS

| | | | |
|---|---|---|---|
| 6,458,374 B1 * | 10/2002 | McCullough | A61K 9/2059 424/423 |
| 9,732,031 B2 | 8/2017 | DeWitt et al. | |
| 2002/0052341 A1 | 5/2002 | Fang et al. | |
| 2015/0126541 A1 | 5/2015 | Tabuteau | |
| 2016/0030420 A1 | 2/2016 | Tabuteau | |
| 2016/0199321 A1 | 7/2016 | Tabuteau | |
| 2016/0263100 A1 | 9/2016 | Tabuteau | |
| 2016/0375008 A1 | 12/2016 | Tabuteau | |
| 2017/0007558 A1 | 1/2017 | Tabuteau | |
| 2017/0014357 A1 | 1/2017 | Tabuteau | |
| 2017/0304230 A1 | 10/2017 | Tabuteau | |
| 2018/0092906 A1 | 4/2018 | Tabuteau | |
| 2019/0216800 A1 | 7/2019 | Tabuteau | |
| 2019/0216801 A1 | 7/2019 | Tabuteau | |
| 2019/0216832 A1 | 7/2019 | Tabuteau | |
| 2020/0093760 A1 | 3/2020 | Tabuteau | |
| 2020/0093761 A1 | 3/2020 | Tabuteau | |

FOREIGN PATENT DOCUMENTS

| | | | | |
|---|---|---|---|---|
| WO | 2012118562 A1 | 9/2012 | | |
| WO | WO-2012118562 A1 * | 9/2012 | ........... | A61K 31/137 |
| WO | 2015095713 A1 | 6/2015 | | |

OTHER PUBLICATIONS

Coles et al., "Stereoselective Metabolism of Bupropion by Cytochrome P4502B6 (CYP2B6) and Human Liver Microsomes", Pharmaceutical Research, 25(6), 1405-1411, Jun. 2008.
Joy et al., "Use of Enantiomeric Bupropion and Hydroxybupropion to Assess CYP2B6 Activity in Glomerular Kidney Diseases", Journal of Clinical Pharmacology, 50 (6), 714-720, Jun. 2010.
Written Opinion of the International Search Authority for PCT/US2014/071519 (corresponding to WO2015095713) dated Feb. 10, 2015.
Malik et al., "Enantioseparation of (RS)-Bupropion and determination of configuration", Journal of Liquid Chromatography & Related Technologies, 41(4), 155-160, 2018.
Masters et al., "Chiral plasma pharmacokinetics and urinary excretion of bupropion and metabolites in healthy volunteers", Journal of Pharmacology and Experimental Therapeutics, 358(2), 230-238, 2016.
Sager et al., "Stereoselective metabolism of bupropion to OH-bupropion, threohydrobupropion, erythrohydrobupropion, and 4'-OH-bupropion in vitro", Drug Metabolism & Disposition, 44(10), 1709-1719, 2016.
Sager et al., "In vitro to in vivo extrapolation of the complex drug-drug interaction of bupropion and its metabolites with CYP2D6; simultaneous reversible inhibition and CYP2D6 downregulation", Biochemical Pharmacology (Amsterdam, Netherlands), 123, 85-96, 2017.
Teitelbaum et al., "Development, validation and application of a comprehensive stereoselective LC/MS-MS assay for bupropion and oxidative, reductive, and glucuronide metabolites in human urine", Journal of Chromatography B: Analytical Technologies in the Biomedical and Life Sciences, 1027, 239-253, 2016.
Teitelbaum et al., "Development and validation of a high-throughput stereoselective LC-MS/MS assay for bupropion, hydroxybupropion, erythrohydrobupropion, and threohydrobupropion in human plasma", Journal of Chromatography B: Analytical Technologies in the Biomedical and Life Sciences, 1017-1018, 101-113, 2016.
Masters et al., "Stereoselective method to quantify bupropion and its three major metabolites, hydroxybupropion, erythro-dihydrobupropion, and threo-dihydrobupropion using HPLC-MS/MS", Journal of Chromatography B: Analytical Technologies in the Biomedical and Life Sciences, 1015-1016, 201-208, 2016.
Bagatin et al., "Molecular docking and panicolytic effect of 8-prenylnaringenin in the elevated T-maze", Chemical & Pharmaceutical Bulletin, 62(12), 1231-1237, 2014.

(Continued)

*Primary Examiner* — Theodore R. West
(74) *Attorney, Agent, or Firm* — Maschoff Brennan; Brent A. Johnson; Yuefen Zhou

(57) ABSTRACT

This disclosure relates to dosage forms containing an enantiomerically enriched or pure bupropion such as enantiomeric excess of (S)-bupropion, enantiomerically enriched (S)-bupropion, or enantiomerically pure (S)-bupropion and methods of using these dosage forms. These dosage forms may be administered to human beings in a reduced amount as compared to the amount of racemic bupropion that would be administered in the same situation.

19 Claims, No Drawings

(56) References Cited

OTHER PUBLICATIONS

Batra et al., "Enantioresolution of (RS)-bupropion by reversed-phase high-performance liquid chromatography using cyanuric chloride based chiral derivatizing reagents having amino acids as chiral auxiliaries", Journal of Liquid Chromatography & Related Technologies, 37(17), 2515-2528, 2014.

Meyer et al., "Formation of threohydrobupropion from bupropion is dependent on 11β-hydroxysteroid dehydrogenase 1", Drug Metabolism & Disposition, 41(9), 1671-1678, 2013.

Bhushan et al., "High-performance liquid chromatographic enantioseparation of (RS)-bupropion using isothiocyanate-based chiral derivatizing reagents", Biomedical Chromatography, 27(8), 956-959, 2013.

Perera et al., "Screening approach, optimization and scale-up for chiral liquid chromatography of cathinones", Journal of Chromatography A, 1269, 189-197, 2012.

Arias et al., "Structural and functional interaction of (±)-2-(N-tert-butylamino)-3'-iodo-4'-azidopropiophenone, a photoreactive bupropion derivative, with nicotinic acetylcholine receptors", Neurochemistry International, 61(8), 1433-1441, 2012.

Zhou et al., "CE enantioseparation of bupropion hydrochloride", Yaowu Fenxi Zazhi, 32(6), 990-993, 972, 2012.

Lai et al., "Novel cyclodextrin chiral stationary phases for high performance liquid chromatography enantioseparation: Effect of cyclodextrin type", Journal of Chromatography A, 1218(33), 5597-5601, 2011.

Castro-Puyana et al., "Sensitized phosphorescence as detection method for the enantioseparation of bupropion by capillary electrophoresis", Electrophoresis, 31(23-24), 3928-3936, 2010.

Castro-Puyana et al., "Enantiomeric separation of bupropion enantiomers by electrokinetic chromatography: Quantitative analysis in pharmaceutical formulations", Journal of Chromatography B: Analytical Technologies in the Biomedical and Life Sciences, 875(1), 260-265, 2008.

Kharasch et al., "Rapid clinical induction of hepatic cytochrome P450 2B6 activity by ritonavir", Antimicrobial Agents and Chemotherapy, 52(5), 1663-1669, 2008.

Kharasch et al., "Stereoselective bupropion hydroxylation as an in vivo phenotypic probe for cytochrome P4502B6 (CYP2B6) activity", Journal of Clinical Pharmacology, 48(4), 464-474, 2008.

Moda et al., "In silico prediction of human plasma protein binding using hologram QSAR", Letters in Drug Design & Discovery, 4(7), 502-509, 2007.

Moda et al., "Hologram QSAR model for the prediction of human oral bioavailability", Bioorganic & Medicinal Chemistry, 15(24), 7738-7745, 2007.

Coles et al., "Stereoselective analysis of bupropion and hydroxybupropion in human plasma and urine by LC/MS/MS", Journal of Chromatography B: Analytical Technologies in the Biomedical and Life Sciences, 857(1), 67-75, 2007.

Liu et al., "Preparation and evaluation of 2,6-di-O-pentyl-β-cyclodextrin bonded silica stationary phase for high performance liquid chromatography", Sepu, 22(6), 630-633, 2004.

Li et al., "Single-isomer sulfated α-cyclodextrins for capillary electrophoresis. Part 2. Hexakis(6-O-sulfo)-α-cyclodextrin: Synthesis, analytical characterization, and initial screening tests", Electrophoresis, 25(9), 1201-1210, 2004.

Busby et al., "Nonaqueous capillary electrophoretic separation of basic enantiomers using octakis(2,3-O-dimethyl-6-O-sulfo)-γ-cyclodextrin, a new, single-isomer chiral resolving agent", Electrophoresis, 23(3), 456-461, 2002.

Fang et al., "Rapid access to enantiopure bupropion and its major metabolite by stereospecific nucleophilic substitution on an α-keto triflate", Tetrahedron: Asymmetry, 11(18), 3659-3663, 2000.

Steuer et al., "Impact of Cytochrome P450 2D6 Function on the Chiral Blood Plasma Pharmacokinetics of 3,4-Methylenedioxymethamphetamine (MDMA) and Its Phase I and II Metabolites in Humans", PLOS One | DOI:10.1371/journal.pone.0150955 Mar. 11, 2016.

U.S. Appl. No. 16/579,305, filed Sep. 23, 2019 First Named Inventor: Herriot Tabuteau Assignee: Axsome Theraputics, Inc.

International Search Report dated Jul. 11, 2019, corresponding to international patent application No. PCT/US2019/019445.

Written opinion of the international searching authority dated Jul. 11, 2019, corresponding to international patent application No. PCT/US2019/019445.

U.S. Appl. No. 16/806,145, filed Mar. 2, 2020, Herriot Tabuteau, Axsome Therapeutics, Inc.

U.S. Appl. No. 16/807,512, filed Mar. 3, 2020, Herriot Tabuteau, Axsome Therapeutics, Inc.

U.S. Appl. No. 16/830,637, filed Mar. 26, 2020, Herriot Tabuteau, Axsome Therapeutics, Inc.

U.S. Appl. No. 16/832,153, filed Mar. 27, 2020, Herriot Tabuteau, Axsome Therapeutics, Inc.

* cited by examiner

DOSAGE FORMS AND METHODS FOR ENANTIOMERICALLY ENRICHED OR PURE BUPROPION

CROSS-REFERENCE TO RELATED APPLICATIONS

This application is a continuation-in-part of U.S. patent application Ser. No. 16/362,434, filed Mar. 22, 2019, which claims the benefit of U.S. provisional patent application Nos. 62/734,021, filed Sep. 20, 2018; and 62/810,880, filed Feb. 26, 2019, all of which are incorporated by reference herein in their entirety.

BACKGROUND

Bupropion is approved for human use as a racemic mixture. It was believed by many that bupropion and its metabolites rapidly racemize in the human body.

SUMMARY

Described herein are dosage forms containing an enantiomeric excess of (S)-bupropion, enantiomerically enriched (S)-bupropion, or enantiomerically pure (S)-bupropion and methods of using those dosage forms. These dosage forms may be administered to human beings in a reduced amount as compared to the amount of racemic bupropion that would be administered in the same situation.

Some embodiments include a method of providing bupropion to the plasma of a human being, comprising: selecting a human patient in need of a pharmacokinetic profile provided by orally administering a reference dosage form containing a first amount of racemic bupropion at a first dosing frequency; and orally administering a dosage form containing a second amount of (S)-bupropion that is at least 95% enantiomerically pure at the first dosing frequency to achieve the same pharmacokinetic profile that would be achieved by administering the reference dosage form at the first dosing frequency; wherein the first dosing frequency is once daily or twice daily; and wherein the second amount is about 20-70%, about 40-60%, about 45-55%, or about 50% of the first amount. For example, if a particular pharmacokinetic profile is achievable by orally administering a dosage form containing 150 mg of racemic bupropion and the second amount is 40-60% of the first amount, the second amount is 60-90 mg. Thus, in this situation, 60-90 mg of (S)-bupropion would be administered once daily to achieve the same pharmacokinetic profile as would be achieved by administering 150 mg of racemic bupropion once daily; or 60-90 mg of (S)-bupropion would be administered twice daily to achieve the same pharmacokinetic profile as would be achieved by administering 150 mg of racemic bupropion twice daily.

For the purposes of this disclosure, if the dosage form containing enantiomerically pure (S)-bupropion is recognized by the FDA as bioequivalent to a dosage form containing racemic bupropion, then the two dosage forms have the same pharmacokinetic profile.

Some embodiments include a method of treating a condition that is treatable with racemic bupropion, comprising: selecting a human patient having the condition that is treatable by orally administering a reference dosage form containing a first amount of racemic bupropion at a first dosing frequency; and orally administering a dosage form containing a second amount of (S)-bupropion that is at least 95% enantiomerically pure at the first dosing frequency to achieve the same therapeutic effect that would be achieved by administering the reference dosage form at the first dosing frequency; wherein the first dosing frequency is once daily or twice daily; and wherein the second amount is about 20-70%, about 40-60%, about 45-55%, or about 50% of the first amount. For example, if a condition is treatable by orally administering a dosage form containing 150 mg of racemic bupropion and the second amount is 40-60% of the first amount, the second amount is 60-90 mg. Thus, in this situation, 60-90 mg of (S)-bupropion would be administered once daily to treat a condition so that the same therapeutic effect is achieved as would be achieved by administering 150 mg of racemic bupropion once daily; or 60-90 mg of (S)-bupropion would be administered twice daily to treat a condition so that the same therapeutic effect is achieved as would be achieved by administering 150 mg of racemic bupropion twice daily.

DETAILED DESCRIPTION

The (S)-bupropion administered to the human being may be enantiomerically pure or enantiomerically enriched. For example, the (S)-bupropion may be at least 70%, at least 80%, at least 85%, at least 90%, at least 95%, at least 96%, at least 97%, at least 98%, at least 99%, at least 99.9%, or at least 99.99% enantiomerically pure, up to (or nearly) 100% enantiomerically pure. (S)-bupropion that is 99.99% enantiomerically pure contains 99.99% (S)-bupropion and 0.001% (R)-bupropion. For convenience, any of the above may be referred to as "(S)-bupropion." This type of dosage form may be useful in treating conditions where increased levels of (S)-bupropion and/or (R,R)-hydroxybupropion are therapeutically beneficial, or for treating human beings in need of treatment with (S)-bupropion and/or (R,R)-hydroxybupropion.

It has been discovered that orally administering (S)-bupropion is bioequivalent or pharmacokinetically equivalent to administering about twice as much racemic bupropion. For example, a 75 mg dose of (S)-bupropion is bioequivalent to a dose of about 150 mg of racemic bupropion.

(S)-bupropion may be administered alone or in combination with another drug. However, for some treatments, use of another drug may not be desirable with (S)-bupropion or (R,R)-hydroxybupropion. For example, (S)-bupropion or (R,R)-hydroxybupropion may be the only compounds needed to treat the condition, additional drugs may not provide any significant benefit, or adding additional drugs may unacceptably increase the risk of adverse events which outweigh any potential benefit that they may provide. Thus, some dosage forms are substantially free of any other drug, and some treatments involve administration of (S)-bupropion without co-administration of any other drug. For example, the dosage form may contain less than 10% by weight, less than 5% by weight, less than 2.5% by weight, less than 1% by weight, or less than 0.1% by weight of any other active pharmaceutical agent, as compared to the weight of the (S)-bupropion or may contain no other drug.

The dosage forms and methods described above may be incorporated into methods for treating a mammal, such as a human being, for providing therapeutically effective plasma levels of (S)-bupropion or one of its metabolites, such as (R,R)-hydroxybupropion, erythrohydroxybupropion, or threohydroxybupropion, or for otherwise providing desirable or enhanced plasma levels or pharmacokinetic properties of (S)-bupropion or one of its metabolites.

For example, the dosage forms and methods may be used to treat neurological disorders, central nervous system disorders, psychiatric disorders, neuropsychiatric disorders, or related conditions.

The term "treating", or "treatment" includes the diagnosis, cure, mitigation, treatment, or prevention of disease in man or other animals, or any activity that otherwise affects the structure or any function of the body of man or other animals.

Administration of (S)-bupropion, e.g. by oral administration, may occur one or more times in a single day, or one or more times a day for multiple days, such as multiple consecutive days. For example, (S)-bupropion may be administered once or twice daily for 1, 2, 3, 4, 5, 6, 7, 8, 9-13, 14, 15-20, 21, 22-27, 28, 29, 30, 31, 32-34, 35, 36-41, 42, 43-48, 49, 50-55, 56, 57-59, 32-59, 60, 61-89, 90, or more consecutive days. The patient may be fasted prior to and/or after oral administration of a dosage form containing (S)-bupropion.

To reduce the risk of seizure or another adverse event, it may be helpful to start with a lower starting daily dose of (S)-bupropion, and then later increasing the dose to a higher target daily dose. A "daily dose" refers to the total amount of bupropion received in a day (e.g., a 75 mg administered in the morning and a 75 mg dose administered in the evening would be a daily dose of 150 mg). For example, a lower starting daily dose is a lower total amount of bupropion received in a day, and a higher target daily dose is a higher total amount of bupropion received in a day. One way to accomplish this is by administering a dosage form containing a lower dose of (S)-bupropion, alone or in combination with other drug, once or twice a day for 1, 2, 3, 4, 5, 6, 7, or more days, followed by treatment with a dosage form containing a higher dose of (S)-bupropion at the same dosing frequency that was used with the lower dose. For example, the dosage form containing a lower dose of (S)-bupropion could be administered once daily on day 1, 2, and 3, and then a higher dose of (S)-bupropion could be administered once daily starting on day 4, and continued once daily for an extended period of time, such as 2, 3, 4, 5, 6, 7, 8, 9-13, 14, 15-20, 21, 22-27, 28, 29, 30, 31, 32-34, 35, 36-41, 42, 43-48, 49, 50-55, 56, 57-59, 32-59, 60, 61-89, 90, or more consecutive days, or for the remainder of the treatment period. Alternatively, the dosage form containing lower dose of (S)-bupropion could be administered twice daily on day 1, 2, and 3, and then a higher dose of (S)-bupropion could be administered twice daily starting on day 4, and continued twice daily for an extended period of time, such as 2, 3, 4, 5, 6, 7, 8, 9-13, 14, 15-20, 21, 22-27, 28, 29, 30, 31, 32-34, 35, 36-41, 42, 43-48, 49, 50-55, 56, 57-59, 32-59, 60, 61-89, 90, or more consecutive days, or for the remainder of the treatment period.

Another way to accomplish this, e.g. increasing from a lower starting daily dose to a higher target dose, is by administering the dosage form containing (S)-bupropion, alone or in combination with other drug, once a day for 1, 2, 3, 4, 5, 6, 7, or more days, followed by twice a day treatment. For example, the dosage form containing (S)-bupropion could be administered once a day on day 1, 2, and 3, and then twice a day starting on day 4, and continued twice a day for an extended period of time, such as 2, 3, 4, 5, 6, 7, 8, 9-13, 14, 15-20, 21, 22-27, 28, 29, 30, 31, 32-34, 35, 36-41, 42, 43-48, 49, 50-55, 56, 57-59, 32-59, 60, 61-89, 90, or more consecutive days, or for the remainder of the treatment period.

(S)-Bupropion has the structure shown below.

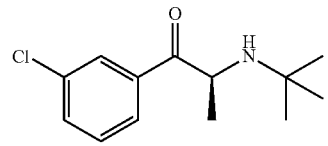 [SMILES: C[C@H](NC(C)(C)C)C(=O)c1cccc(Cl)c1]

Unless otherwise indicated, any reference to a compound herein, such as (S)-bupropion, by structure, name, or any other means, includes pharmaceutically acceptable salts; alternate solid forms, such as polymorphs, crystals, solvates, hydrates, etc.; tautomers; isotopically-enriched compounds (e.g. deuterium enriched bupropion); or any chemical species that may rapidly convert to a compound described herein under conditions in which the compounds are used as described herein.

For dosage forms comprising (S)-bupropion, such as at least 95%, at least 97%, at least 99%, or at least 99.9% enantiomerically pure bupropion, any suitable amount of (S)-bupropion may be used. In some embodiments, a dosage form contains at least about 10 mg, at least about 20 mg, at least about 30 mg, at least about 50 mg, at least about 60 mg, at least about 70 mg, at least about 80 mg, at least about 90 mg, at least about 100 mg, about 1-50 mg, about 50-150 mg, about 50-100 mg, about 100-150 mg, 150-200 mg, about 100-200 mg, about 1-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-110 mg, about 100-120 mg, about 120-150 mg, about 1-30 mg, about 20-50 mg, about 50-80 mg, about 80-120 mg, about 100-150 mg, about 150-180 mg, about 180-200 mg, about 70-95 mg, about 50-70 mg, about 60-80 mg, about 60-90 mg, about 70-80 mg, about 70-74 mg, about 72-76 mg, about 74-76 mg, about 74-78 mg, about 70-90 mg, about 70 mg, about 75 mg, about 80 mg, about 100 mg of (S)-bupropion, or any amount in a range bounded by any of these values. Ranges of amounts of (S)-Bu obtained by combining any of the ranges or endpoints above are also contemplated, especially if the range obtained encompasses, or is near, one or more the following values for the amount of (S)-bupropion in the dosage form: about 60 mg, about 75 mg, or about 90 mg. These are values that are believed to potentially be of particular utility. A dosage form containing an amount of (S)-bupropion listed above may be administered once, twice, or three times a day for a daily dose that is 1, 2, or 3 times that of any dose amount or any dose range listed above, e.g. 2 times 50-100 mg for a daily dose of 100-200 mg, or 3 times 50-100 mg for a daily dose of 150-300 mg. Any daily dose obtained by combining any of the dose ranges or endpoints above and multiplying that result by 1, 2, or 3 are also contemplated, especially if the range obtained encompasses, or is near, one or more the following values: about 120 mg, about 150 mg, or about 180 mg. These are values that are believed to potentially be of somewhat more interest for average sized adults. Lower doses, such as about 1-50 mg or about 1-70 mg, given once or twice a day, may be somewhat more useful for the treatment of children. Higher doses, e.g. over about 100 mg, given twice or three times a day, may be somewhat more useful for the treatment of larger adults.

Because (S)-bupropion is unexpectedly the primary source of the bupropion and bupropion metabolites present in the blood, the amount of (S)-bupropion administered to a person can be considerably lower than the amount of racemic bupropion (or (R)-bupropion) that would be administered to treat the same condition with the same effect. For example, if the amount of racemic bupropion administered to treat a condition is 150 mg, a lower amount of (S)-bupropion such as 5-50% or 20-70% of that amount, i.e. 30-105 mg, can be administered to achieve a similar effect. In some embodiments, the amount of (S)-bupropion administered is selected to be about 5-70%, about 5-50%, about 20-70%, about 5-10%, about 10-20%, about 20-30%, about 30-40%, about 40-50%, about 50-60%, about 60-70%, about 20-50%, about 40-70%, about 40-60%, about 40-45%, or about 45-55%, of the amount of racemic bupropion that would be administered to treat the same human being for the same condition Some solid compositions may comprise at least about 5%, at least about 10%, at least about 20%, at least about 50%, at least about 70%, at least about 80%, about 10-30%, about 30-50%, about 50-80%, about 80-95%, about 10-50%, about 30-70%, or about 50-90% of (S)-bupropion by weight.

In some embodiments, the dosage form may be free, or substantially free, of any active pharmaceutical ingredients, or drugs, other than the (S)-bupropion. For example, the dosage form may contain less than 10% by weight, less than 5% by weight, less than 1% by weight, or less than 0.1% by weight of any other active pharmaceutical ingredient, as compared to the weight of the (S)-bupropion.

Administering (S)-bupropion may be useful in increasing plasma levels of (S)-bupropion by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, about 5-20 fold, at least about 10-fold, at least about 20-fold, at least about 50-fold, at least about 100-fold, at least about 150-fold, at least about 200-fold, or more, about 10-15 fold, about 10-25 fold, about 5-20 fold, about 20-30 fold, about 30-40 fold, about 40-50 fold, about 50-60 fold, about 60-70 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to the plasma level of (R)-bupropion obtained by administering a dosage form containing the same amount of (R)-bupropion to the human being.

In some embodiments, the method is effective in increasing the $AUC_{0-12}$, such as the average $AUC_{0-12}$, the mean $AUC_{0-12}$, the median $AUC_{0-12}$, or the $AUC_{0-12}$ of an individual, of (S)-bupropion by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, at least about 8-fold, at least about 10-fold, about 10-fold, at least about 15-fold, at least about 20-fold, at least about 25-fold, at least about 50-fold, at least about 100-fold, at least about 150-fold, at least about 200-fold, or more, about 10-15 fold, about 10-25 fold, about 5-20 fold, about 20-30 fold, about 30-40 fold, about 40-50 fold, about 50-60 fold, about 60-70 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to the $AUC_{0-12}$ of (R)-bupropion obtained administering a dosage form containing the same amount of (R)-bupropion to the human being.

In some embodiments, the method achieves an $AUC_{0-12}$, such as the average $AUC_{0-12}$, the mean $AUC_{0-12}$, the median $AUC_{0-12}$, or the $AUC_{0-12}$ of an individual, of (S)-bupropion that is at least about 300 ng·hr/mL, at least about 400 ng·hr/mL, at least about 500 ng·hr/mL, at least about 600 ng·hr/mL, at least about 700 ng·hr/mL, at least about 750 ng·hr/mL, at least about 800 ng·hr/mL, at least about 850 ng·hr/mL, at least about 900 ng·hr/mL, at least about 950 ng·hr/mL, at least about 1,000 ng·hr/mL, at least about 1,100 ng·hr/mL, up to about 1,200 ng·hr/mL, up to about 1,300 ng·hr/mL, up to about 1,400 ng·hr/mL, up to about 1,500 ng·hr/mL, up to about 1,600 ng·hr/mL, up to about 1,700 ng·hr/mL, up to about 1,800 ng·hr/mL, about 300-400 ng·hr/mL, about 400-500 ng·hr/mL, about 500-600 ng·hr/mL, about 600-700 ng·hr/mL, about 700-800 ng·hr/mL, about 800-900 ng·hr/mL, about 900-1,000 ng·hr/mL, about 1,000-1,100 ng·hr/mL, about 1,100-1,200 ng·hr/mL, about 1,200-1,300 ng·hr/mL, about 1,300-1,400 ng·hr/mL, about 1,400-1,500 ng·hr/mL, about 1,500-1,600 ng·hr/mL, about 1,600-1,700 ng·hr/mL, about 1,700-1,800 ng·hr/mL, about 300-600 ng·hr/mL, about 600-900 ng·hr/mL, about 900-1,200 ng·hr/mL, about 1,200-1,500 ng·hr/mL, about 1,500-1,800 ng·hr/mL, about 300-800 ng·hr/mL, about 800-1,300 ng·hr/mL, about 1,300-1,800 ng·hr/mL, or about 300-1,800 ng·hr/mL. Ranges of $AUC_{0-12}$ obtained by combining any of the ranges or endpoints above are also contemplated, especially if the range obtained encompasses, or is near, one or more the following values for $AUC_{0-12}$: 350 ng·hr/mL, 400 ng·hr/mL, 750 ng·hr/mL, or 900 ng·hr/mL. These are values that are believed to potentially be of particular utility.

In some embodiments, the method is effective in increasing the $C_{max}$, such as the average $C_{max}$, the mean $C_{max}$, the median $C_{max}$, or the $C_{max}$ of an individual, of (S)-bupropion by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, at least about 8-fold, about 5-20 fold, at least about 10-fold, about 10-fold, at least about 20-fold, at least about 25-fold, at least about 50-fold, at least about 100-fold, at least about 150-fold, at least about 200-fold, or more, about 10-15 fold, about 10-25 fold, about 5-20 fold, about 20-30 fold, about 30-40 fold, about 40-50 fold, about 50-60 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

In some embodiments, the method achieves a $C_{max}$, such as the average $C_{max}$, the mean $C_{max}$, the median $C_{max}$, or the $C_{max}$ of an individual, of (S)-bupropion that is at least about 30 ng/mL, at least about 50 ng/mL, at least about 60 ng/mL, at least about 70 ng/mL, at least about 80 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, up to about 130 ng/mL, up to about 140 ng/mL, up to about 150 ng/mL, up to about 160 ng/mL, up to about 170 ng/mL, up to about 180 ng/mL, up to about 190 ng/mL, up to about 200 ng/mL, up to about 210 ng/mL, up to about 220 ng/mL, about 30-40 ng/mL, about 40-50 ng/mL, about 50-60 ng/mL, about 60-70 ng/mL, about 70-80 ng/mL, bout 80-90 ng/mL, about 90-100 ng/mL, about 100-110 ng/mL, about 110-120 ng/mL, about 120-130 ng/mL, about 130-140 ng/mL, about 140-150 ng/mL, about 150-160 ng/mL, about 160-170 ng/mL, about 170-180 ng/mL, about 180-190 ng/mL, about 190-200 ng/mL, about 200-210 ng/mL, about 210-220 ng/mL, about 50-70 ng/mL, about 70-90 ng/mL, about 30-60 ng/mL, about 60-90 ng/mL, about 90-120 ng/mL, about 120-160 ng/mL, about 160-220 ng/mL, about 30-90 ng/mL, about 90-150 ng/mL, about 150-220 ng/mL, about 30-110 ng/mL, about 110-220 ng/mL, or about 30-220 ng/mL. Ranges of $C_{max}$ obtained by combining any of the ranges or endpoints above are also contemplated, especially if the range obtained encompasses, or is near, one or more the following values for $C_{max}$: 45 ng/mL, 90 ng/mL, 125 ng/mL, 150 ng/mL, or 180 ng/mL. These are values that are believed to potentially be of particular utility.

In some embodiments, the method is effective in increasing the $C_{min}$, such as the average $C_{min}$, the mean $C_{min}$, the median $C_{min}$, or the $C_{min}$ of an individual, of (S)-bupropion by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, at least about 8-fold, at least about 10-fold, at least about 20-fold, at least about 50-fold, at least about 100-fold, at least about 150-fold, at least about 200-fold, or more, about 10-15 fold, about 10-25 fold, about 5-20 fold, about 20-30 fold, about 30-40 fold, about 40-50 fold, about 50-60 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

In some embodiments, the method achieves a $C_{min}$, such as the average $C_{min}$, the mean $C_{min}$, the median $C_{min}$, or the $C_{min}$ of an individual, of (S)-bupropion that is at least about 20 ng/mL, at least about 25 ng/mL, at least about 30 ng/mL, at least about 35 ng/mL, at least about 40 ng/mL, about 20-60 ng/mL, about 20-25 ng/mL, about 25-30 ng/mL, about 30-35 ng/mL, about 35-40 ng/mL, about 30-40 ng/mL, about 40-45 ng/mL, about 45-50 ng/mL, about 30-50 ng/mL, about 40-50 ng/mL, or about 50-60 ng/mL. Ranges of $C_{min}$ obtained by combining any of the ranges or endpoints above are also contemplated, especially if the range obtained encompasses, or is near, one or more the following values for $C_{min}$: 20 ng/mL, 30 ng/mL, 40 ng/mL, or 50 ng/mL. These are values that are believed to potentially be of particular utility.

Administering (S)-bupropion may be useful in increasing plasma levels of (R,R)-hydroxybupropion, by at least about 1.1-fold, at least about 1.5-fold, at least about 2-fold, at least about 3-fold, at least about 5-fold, at least about 10-fold, at least about 15-fold, at least about 20-fold, at least about 40-fold, at least about 50-fold, at least about 100-fold, at least about 150-fold, at least about 200-fold, or more, about 5-10 fold, about 5-25 fold, about 5-20 fold, about 20-30 fold, about 30-40 fold, about 40-50 fold, about 50-60 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

Administering (S)-bupropion may be useful in increasing the $AUC_{0-12}$, such as the average $AUC_{0-12}$, the mean $AUC_{0-12}$, the median $AUC_{0-12}$, or the $AUC_{0-12}$ of an individual, of (R,R)-hydroxybupropion, by at least about 1.1-fold, at least about 1.5-fold, at least about 2-fold, at least about 3-fold, at least about 5-fold, about 6-fold, at least about 10-fold, at least about 15-fold, at least about 20-fold, at least about 40-fold, at least about 50-fold, at least about 100-fold, at least about 150-fold, at least about 200-fold, or more, about 5-10 fold, about 5-25 fold, about 5-20 fold, about 20-30 fold, about 30-40 fold, about 40-50 fold, about 50-60 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

In some embodiments, the method achieves an $AUC_{0-12}$, such as the average $AUC_{0-12}$, the mean $AUC_{0-12}$, the median $AUC_{0-12}$, or the $AUC_{0-12}$ of an individual, of (R,R)-hydroxybupropion that is at least about 1,000 ng·hr/mL, at least about 3,000 ng·hr/mL, at least about 4,000 ng·hr/mL, at least about 6,000 ng·hr/mL, at least about 7,000 ng·hr/mL, at least about 7,500 ng·hr/mL, at least about 8,000 ng·hr/mL, at least about 8,500 ng·hr/mL, at least about 9,000 ng·hr/mL, at least about 9,500 ng·hr/mL, at least about 10,000 ng·hr/mL, at least about 12,000 ng·hr/mL, at least about 13,000 ng·hr/mL, about 4,000-6,000 ng·hr/mL, about 6,000-8,000 ng·hr/mL, about 8,000-10,000 ng·hr/mL, about 10,000-12,000 ng·hr/mL, about 12,000-14,000 ng·hr/mL, about 14,000-16,000 ng·hr/mL, about 16,000-18,000 ng·hr/mL, about 18,000-20,000 ng·hr/mL, about 20,000-22,000 ng·hr/mL, about 22,000-24,000 ng·hr/mL, about 4,000-10,000 ng·hr/mL, about 10,000-16,000 ng·hr/mL, about 16,000-24,000 ng·hr/mL, about 4,000-24,000 ng·hr/mL, up to about 14,000 ng·hr/mL, up to about 16,000 ng·hr/mL, up to about 18,000 ng·hr/mL, up to about 20,000 ng·hr/mL, up to about 22,000 ng·hr/mL, up to about 24,000 ng·hr/mL, or up to about 30,000 ng·hr/mL. Ranges of $AUC_{0-12}$ obtained by combining any of the ranges or endpoints above are also contemplated, especially if the range obtained encompasses, or is near, one or more the following values for $AUC_{0-12}$: 4,000 ng·hr/mL, 5,000 ng/mL, 10,000 ng·hr/mL, 16,000 ng·hr/mL, or 22,000 ng·hr/mL. These are values that are believed to potentially be of particular utility.

Administering (S)-bupropion may be useful in increasing the $C_{max}$, such as the average $C_{max}$, the mean $C_{max}$, the median $C_{max}$, or the $C_{max}$ of an individual, of (R,R)-hydroxybupropion, by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, about 6-fold, at least about 10-fold, at least about 20-fold, at least about 50-fold, at least about 100-fold, at least about 150-fold, at least about 200-fold, or more, about 5-10 fold, about 10-20 fold, about 5-20 fold, about 20-30 fold, about 30-40 fold, about 40-50 fold, about 50-60 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

In some embodiments, the method achieves a $C_{max}$, such as the average $C_{max}$, the mean $C_{max}$, the median $C_{max}$, or the $C_{max}$ of an individual, of (R,R)-hydroxybupropion that is at least about 150 ng/mL, at least about 200 at least about 300 ng/mL, at least about 400 ng/mL, at least about 500 ng/mL, at least about 600 ng/mL, at least about 700 ng/mL, at least about 800 ng/mL, at least about 900 ng/mL, at least about 1,000 ng/mL, at least about 1,100 ng/mL, at least about 1,200 ng/mL, at least about 1,300 ng/mL, up to about 1,400 ng/mL, up to about 1,500 ng/mL, up to about 1,600 ng/mL, up to about 1,700 ng/mL, up to about 1,800 ng/mL, up to about 1,900 ng/mL, up to about 2,000 ng/mL, up to about 2,100 ng/mL, up to about 2,200 ng/mL, up to about 2,300 ng/mL, about 300-400 ng/mL, about 400-500 ng/mL, about 500-600 ng/mL, about 600-700 ng/mL, about 700-800 ng/mL, about 800-900 ng/mL, about 900-1,000 ng/mL, about 1,000-1,100 ng/mL, about 1,100-1,200 ng/mL, about 1,200-1,300 ng/mL, about 1,300-1,400 ng/mL, about 1,400-1,500 ng/mL, about 1,500-1,600 ng/mL, about 1,600-1,700 ng/mL, about 1,700-1,800 ng/mL, about 1,800-1,900 ng/mL, about 1,900-2,000 ng/mL, about 2,000-2,100 ng/mL, about 2,100-2,200 ng/mL, about 2,200-2,300 ng/mL, about 300-800 ng/mL, about 800-1,300 ng/mL, about 1,300-2,300 ng/mL, or about 300-2,300 ng/mL. Ranges of $C_{max}$ obtained by combining any of the ranges or endpoints above are also contemplated, especially if the range obtained encompasses, or is near, one or more of the following values for $C_{max}$: 400 ng/mL, 950 ng/mL, 1,500 ng/mL, or 2,100 ng/mL. These are values that are believed to potentially be of particular utility.

Administering (S)-bupropion may be useful in increasing the $C_{min}$, such as the average $C_{min}$, the mean $C_{min}$, the median $C_{min}$, or the $C_{min}$ of an individual, of (R,R)-hydroxybupropion, by at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 2.5-fold, at least about 3-fold, at least about 4-fold, at least about 5-fold, at least about 10-fold, at least about 20-fold, at least about 50-fold, at least about 60-fold, at least about 100-fold, at least about 150-fold, at least about 200-fold, or more, about 1-5 fold, about 5-10 fold, about 5-20 fold, about 20-30 fold, about 30-40 fold, about 40-50 fold, about 50-60 fold, about 60-70 fold, about 70-80 fold, about 80-90 fold, about 90-100 fold, about 100-110 fold, about 110-120 fold, about 120-130 fold, about 130-140 fold, about 140-150 fold, about 150-160 fold, about 160-170 fold, about 170-180 fold, about 180-190 fold, or about 190-200 fold, as compared to administering a dosage form containing the same amount of (R)-bupropion to the human being.

In some embodiments, the method achieves a $C_{min}$, such as the average $C_{min}$, the mean $C_{min}$, the median $C_{min}$, or the $C_{min}$ of an individual, of (R,R)-hydroxybupropion that is at least about 150 ng/mL, at least about 200 ng/mL, at least about 300 ng/mL, at least about 400 ng/mL, at least about 500 ng/mL, at least about 600 ng/mL, at least about 700 ng/mL, at least about 800 ng/mL, at least about 900 ng/mL, at least about 1,000 ng/mL, at least about 1,100 ng/mL, at least about 1,200 ng/mL, up to about 1,300 ng/mL, up to about 1,400 ng/mL, up to about 1,500 ng/mL, up to about 1,600 ng/mL, up to about 1,700 ng/mL, up to about 1,800 ng/mL, up to about 1,900 ng/mL, up to about 2,000 ng/mL, up to about 2,100 ng/mL, up to about 2,200 ng/mL, up to about 2,300 ng/mL, about 200-300 ng/mL, about 300-400 ng/mL, about 400-500 ng/mL, about 500-600 ng/mL, about 600-700 ng/mL, about 700-800 ng/mL, about 800-900 ng/mL, about 900-1,000 ng/mL, about 1,000-1,100 ng/mL, about 1,100-1,200 ng/mL, about 1,200-1,300 ng/mL, about 1,300-1,400 ng/mL, about 1,400-1,500 ng/mL, about 1,500-1,600 ng/mL, about 300-700 ng/mL, about 700-1,100 ng/mL, or about 1,100-1,600 ng/mL. Ranges of $C_{min}$ obtained by combining any of the ranges or endpoints above are also contemplated, especially if the range obtained encompasses, or is near, one or more of the following values for $C_{min}$: 350 ng/mL, 600 ng/mL, 700 ng/mL, 1,000 ng/mL, or 1,400 ng/mL. These are values that are believed to potentially be of particular utility.

Administering (S)-bupropion to a human being may result in (R,R)-hydroxybupropion being at least 90%, 95%, 97%, 97.2%, 97.4%, 97.6%, 97.8%, or 98% of the total of amount of (R,R)-hydroxybupropion and (S,S)-hydroxybupropion present in the plasma of the human being.

In some embodiments, the method achieves an $AUC_{0-12}$, such as the average $AUC_{0-12}$, the mean $AUC_{0-12}$, the median $AUC_{0-12}$, or the $AUC_{0-12}$ of an individual, of erythrohydroxybupropion that is at least about 500 ng·hr/mL, at least about 600 ng·hr/mL, at least about 800 ng·hr/mL, at least about 1,000 ng·hr/mL, at least about 1,200 ng·hr/mL, up to about 1,400 ng·hr/mL, up to about 1,600 ng·hr/mL, up to about 1,800 ng·hr/mL, up to about 2,000 ng·hr/mL, up to about 2,200 ng·hr/mL, up to about 2,400 ng·hr/mL, up to about 2,600 ng·hr/mL, up to about 2,800 ng·hr/mL, up to about 3,000 ng·hr/mL, about 500-600 ng·hr/mL, about 600-800 ng·hr/mL, about 800-1,000 ng·hr/mL, about 1,000-1,200 ng·hr/mL, about 1,200-1,400 ng·hr/mL, about 1,400-1,600 ng·hr/mL, about 1,600-1,800 ng·hr/mL, about 1,800-2,000 ng·hr/mL, about 2,000-2,200 ng·hr/mL, about 2,200-2,400 ng·hr/mL, about 2,400-2,600 ng·hr/mL, about 2,600-2,800 ng·hr/mL, about 2,800-3,000 ng·hr/mL, about 500-1,000 ng·hr/mL, about 1,000-1,500 ng·hr/mL, about 1,500-2,000 ng·hr/mL, about 2,000-2,500 ng·hr/mL, about 2,500-3,000 ng·hr/mL, about 500-1,500 ng·hr/mL, about 1,500-3,000 ng·hr/mL, about 2,000-3,000 ng·hr/mL, or about 500-3,000 ng·hr/mL. Ranges of $AUC_{0-12}$ obtained by combining any of the ranges or endpoints above are also contemplated, especially if the range obtained encompasses, or is near, one or more the following values for $AUC_{0-12}$: 500 ng·hr/mL, 1,300 ng·hr/mL, 1,800 ng·hr/mL, or 2,600 ng·hr/mL. These are values that are believed to potentially be of particular utility.

In some embodiments, the method achieves a $C_{max}$, such as the average $C_{max}$, the mean $C_{max}$, the median $C_{max}$, or the $C_{max}$ of an individual, of erythrohydroxybupropion that is at least about 40 ng/mL, at least about 60 ng/mL, at least about 80 ng/mL, at least about 90 ng/mL, at least about 100 ng/mL, at least about 120 ng/mL, at least about 140 ng/mL, up to about 160 ng/mL, up to about 180 ng/mL, up to about 200 ng/mL, up to about 220 ng/mL, up to about 240 ng/mL, up to about 260 ng/mL, up to about 280 ng/mL, about 40-60 ng/mL, about 60-80 ng/mL, about 80-100 ng/mL, about 100-120 ng/mL, about 120-140 ng/mL, about 140-160 ng/mL, about 160-180 ng/mL, about 180-200 ng/mL, about 200-220 ng/mL, about 220-240 ng/mL, about 240-260 ng/mL, about 260-280 ng/mL, about 280-300 ng/mL, about 40-100 ng/mL, about 100-150 ng/mL, about 150-200 ng/mL, about 200-250 ng/mL, about 250-280 ng/mL, about 40-120 ng/mL, about 120-200 ng/mL, about 200-280 ng/mL, or about 40-280 ng/mL. Ranges of $C_{max}$ obtained by combining any of the ranges or endpoints above are also contemplated, especially if the range obtained encompasses, or is near, one or more the following values for $C_{max}$: 60 ng/mL, 120 ng/mL, 200 ng/mL, or 240 ng/mL. These are the values that are believed to potentially be of particular utility.

In some embodiments, the method achieves an $AUC_{0-12}$, such as the average $AUC_{0-12}$, the mean $AUC_{0-12}$, the median $AUC_{0-12}$, or the $AUC_{0-12}$ of an individual, of threohydroxybupropion that is at least about 2,000 ng·hr/mL, at least about 3,000 ng·hr/mL, at least about 4,000 ng·hr/mL, at least about 5,000 ng·hr/mL, at least about 6,000 ng·hr/mL, at least about 7,000 ng·hr/mL, up to about 8,000 ng·hr/mL, up to about 9,000 ng·hr/mL, up to about 10,000 ng·hr/mL, up to about 11,000 ng·hr/mL, up to about 12,000 ng·hr/mL, up to about 13,000 ng·hr/mL, up to about 14,000 ng·hr/mL, up to about 15,000 ng·hr/mL, about 2,000-15,000 ng·hr/mL, about 2,000-3,000 ng·hr/mL, about 3,000-4,000 ng·hr/mL, about 4,000-5,000 ng·hr/mL, about 5,000-6,000 ng·hr/mL, about 6,000-7,000 ng·hr/mL, about 7,000-8,000 ng·hr/mL, about 8,000-9,000 ng·hr/mL, about 9,000-10,000 ng·hr/mL, about 10,000-11,000 ng·hr/mL, about 11,000-12,000 ng·hr/mL, about 12,000-13,000 ng·hr/mL, about 13,000-14,000 ng·hr/mL, about 14,000-15,000 ng·hr/mL, about 2,000-6,000 ng·hr/mL, about 6,000-10,000 ng·hr/mL, about 10,000-15,000 ng·hr/mL, about 2,000-9,000 ng·hr/mL, or about 9,000-15,000 ng·hr/mL. Ranges of $AUC_{0-12}$ obtained by combining any of the ranges or endpoints above are also contemplated, especially if the range obtained encompasses, or is near, one or more the following values for $AUC_{0-12}$: 3,000 ng·hr/mL, 6,000 ng·hr/mL, 8,000 ng·hr/mL, or 12,000 ng·hr/mL. These are the values that are believed to potentially be of particular utility.

In some embodiments, the method achieves a $C_{max}$, such as the average $C_{max}$, the mean $C_{max}$, the median $C_{max}$, or the $C_{max}$ of an individual, of threohydroxybupropion that is at least about 200 ng/mL, at least about 300 ng/mL, at least about 400 ng/mL, at least about 450 ng/mL, at least about 500 ng/mL, at least about 600 ng/mL, at least about 700 ng/mL, up to about 800 ng/mL, up to about 900 ng/mL, up to about 1,000 ng/mL, up to about 1,100 ng/mL, up to about 1,200 ng/mL, up to about 1,300 ng/mL, up to about 1,400 ng/mL, about 200-300 ng/mL, about 300-400 ng/mL, about 400-500 ng/mL, about 500-600 ng/mL, about 600-700 ng/mL, about 700-800 ng/mL, about 800-900 ng/mL, about 900-1000 ng/mL, about 1,000-1,100 ng/mL, about 1,100-1,200 ng/mL, about 1,200-1,300 ng/mL, about 1,300-1,400 ng/mL, about 200-500 ng/mL, about 500-800 ng/mL, about 800-1,100 ng/mL, about 1,100-1,400 ng/mL, about 200-800 ng/mL, about 800-1400 ng/mL, or about 200-1,400 ng/mL. Ranges of $C_{max}$ obtained by combining any of the ranges or endpoints above are also contemplated, especially if the range obtained encompasses, or is near, one or more the following values for Cmax: 300 ng/mL, 600 ng/mL, 900 ng/mL, or 1,200 ng/mL. These are values that are believed to potentially be of particular utility.

Unless otherwise indicated, any reference to a compound herein, such as (S)-bupropion, by structure, name, or any other means, includes pharmaceutically acceptable salts; alternate solid forms, such as polymorphs, crystals, solvates, hydrates, etc.; tautomers; deuterium-modified compounds; or any chemical species that may rapidly convert to a compound described herein under conditions in which the compounds are used as described herein.

(S)-Bupropion, alone or in a combination with another drug may be combined with a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration, and standard pharmaceutical practice.

(S)-bupropion drug may be administered to a human patient in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal; ophthalmic; sublingual; and buccal, and topically including ophthalmic; dermal; ocular; rectal; nasal; etc.

(S)-bupropion may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

Tablets, troches, pills, capsules and the like containing (S)-bupropion may also contain one or more of the following: a binder such as gum tragacanth, acacia, corn starch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.

Some compositions or dosage forms may be a liquid or may comprise a solid phase dispersed in a liquid.

(S)-bupropion may be formulated for parental or intraperitoneal administration. Solutions of the active compounds as free bases or pharmacologically acceptable salts can be prepared in water suitably mixed with a surfactant. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

Some embodiments include administration of a tablet that contains (S)-Bupropion in a form that provides sustained release of (S)-Bupropion. A sustained release dosage form containing (S)-Bupropion may have a $T_{max}$ of about 2-4 hours, 4-6 hours, or 6-8 hours. While there are many ways that sustained release of bupropion may be achieved, in some embodiments, (S)-Bupropion or (R)-bupropion is combined with a sustained release polymer, such as an acrylic acid or a methacrylic acid copolymer or an ester thereof, e.g. a methyl methacrylate copolymer, an ethoxyethyl methacrylate, cyanoethyl methacrylate, aminoalkyl methacrylate copolymer, poly(acrylic acid), poly(methacrylic acid), methacrylic acid alkylamine copolymer, poly (methyl methacrylate), poly(methacrylic acid) (anhydride), polyacrylamide, poly(methacrylic acid anhydride), a glycidyl methacrylate copolymers; a quaternized aminoalkyl ester or an aminoalkyl amide of acrylic acid and/or methacrylic acid, for example β-methacryloxyethyltrimethylammonium methosulfate, β-acryloxypropyltrimethylammonium chloride, and trimethylaminomethylmethacrylamide methosulfate, quaternized vinyl-substituted nitrogen heterocycles such as methyl-vinyl pyridinium salts, vinyl esters of quaternized amino carboxylic acids, styryltrialkyl ammonium salts, benzyldimethylammoniumethylmethacrylate chloride, diethylmethylammoniumethyl-acrylate, diethylmethylammoniumethylmethacrylate methosulfate, N-trimethylammoniumpropylmethacrylamide chloride, N-trimethylammonium-2,2-dimethylpropyl-1-methacrylate chloride; a cellulose derivative such as a carboxyalkylcellulose (e.g. carboxymethylcellulose), hydroxypropyl methylcellulose, etc. In some embodiments, the sustained release polymer is hydroxypropyl methylcellulose. For example, particles of (S)-Bupropion could be blended with microcrystalline cellulose and hydroxypropyl methylcellulose (e.g., METHOCEL®) to form a mixture of blended powders.

Examples of neurological disorders or central nervous system disorders that may be treated by administering (S)-bupropion (including administering (S)-bupropion to achieve therapeutic plasma levels of one of its metabolites, such as (R,R)-hydroxybupropion) include, but are not limited to: affective disorders, psychiatric disorders, cerebral function disorders, movement disorders, dementias, motor neuron diseases, neurodegenerative diseases, seizure disorders, and headaches.

Affective disorders that may be treated by administering (S)-bupropion (including administering (S)-bupropion to achieve therapeutic plasma levels of one of its metabolites, such as (R,R)-hydroxybupropion) include, but are not limited to, depression, major depression, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Some patients, even after treatment with medications such as antidepressants, may have an inadequate or no response to the treatment. Treatment resistant depression (TRD), or treatment-refractory depression, is a condition generally associated with patients who have failed treatment with at least two antidepressants. Part of the diagnosis for TRD is for the patient to have had an inadequate response to treatment with the antidepressants after an adequate dose and adequate course. TRD may be more difficult to treat due to the comorbidity of other medical or psychological illnesses, such as drug/alcohol abuse or eating disorders, or TRD being misdiagnosed. Some TRD patients have had an inadequate response to 1, 2, 3, or more adequate antidepressant treatment trials or have failed or had an inadequate response to 1, 2, 3, or more prior antidepressant treatments.

In some embodiments, a patient being treated for treatment resistant depression has failed treatment with at least 1, 2, 3, 4, 5, 6, 7, 8, 9, 10, or more antidepressant therapies.

Measures of treatment effect that may be improved by administering (S)-bupropion (including administering (S)-bupropion to achieve therapeutic plasma levels of one of its metabolites, such as (R,R)-hydroxybupropion) include, but are not limited to: Montgomery-Asberg Depression Rating Scale (MADRS), Quality of Life Enjoyment and Satisfaction Questionnaire Short Form, Range of Impaired Functioning Tool, Sheehan Disability Scale, Patient Rated Inventory of Side Effects (PRISE), Columbia-Suicide Severity Rating Scale (C-SSRS), Quick Inventory of Depressive Symptomatology, Self-Report (QID(S)-SR), Clinical Global Impression (CGI) scale, Massachusetts General Hospital Cognitive and Physical Functioning Questionnaire (CPFQ), 17-item Hamilton Rating Scale for Depression (HAM-D17), Massachusetts General Hospital Antidepressant Treatment Response Questionnaire (MGH ATRQ), 16-item Quick Inventory of Depressive Symptomatology—Self Report (QID(S)-5R16), Sheehan Disability Scale (SDS), Clinical Global Impression of Severity of Illness (CGI-S), Clinical Global Impression of Change (CGI-C), EuroQOL 5 Dimension 5 Level (EQ-5D-5L), Patient Global Impression of Change (PGIC), 7-item Generalized Anxiety Disorder (GAD-7), Clinical Global Impressions—Improvement (CGI-I). Sheehan Disability Scale (SDS). 16-item Quick Inventory of Depressive Symptomatology—Self Report (QID(S)-5R16), Hamilton Anxiety Scale (HAM-A), Massachusetts General Hospital Cognitive and Physical Functioning Questionnaire (CPFQ), CPFQ—Cognitive subscales (Items 4 to 7), Brief Psychiatric Rating Scale (BPRS), etc.; Digit Symbol Substitution Test (DSST), Rey Auditory Verbal Learning Task (RAVLT), Trail Making Test (TMT), Stroop Colour Naming Test (STROOP), Simple Reaction Time (SRT), Choice Reaction Time (CRT), etc.

Patients who may benefit from the treatments described herein include pediatric patients, such as patients under about 18 years of age, about 0-5 years of age, about 5-10 years of age, about 10-12 years of age, or about 12-18 years of age, adult patients, such as patients having an age of about 18-65 years; about 18-30 years; about 30-50 years; about 50-65 years, and elderly patients, such as patients over 65 years of age; about 65-75 years of age; about 75-90 years of age; or over 90 years of age.

Treatment of TRD by administering (S)-bupropion (including administering (S)-bupropion to achieve therapeutic plasma levels of one of its metabolites, such as (R,R)-hydroxybupropion) may result in a reduction of depressive symptoms of at least about 5%, at least about 10%, at least about 20%, at least about 30%, at least about 40%, at least about 50%, at least about 60%, at least about 70%, at least about 80%, at least about 90%, up to about 100%, or any other reduction percentage in a range bounded by any of these values.

Psychiatric disorders that may be treated by administering (S)-bupropion (including administering (S)-bupropion to achieve therapeutic plasma levels of one of its metabolites, such as (R,R)-hydroxybupropion) include, but are not limited to, anxiety disorders, such as phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Agitation associated with Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

In some embodiments, treatment of agitation associated with Alzheimer's disease by administering (S)-bupropion (including administering (S)-bupropion to achieve therapeutic plasma levels of one of its metabolites, such as (R,R)-hydroxybupropion) may result in a reduction of agitation-related symptoms of at least about 5%, at least about 10%, at least about 20%, at least about 30%, at least about 40%, at least about 50%, at least about 60%, at least about 70%, at least about 80%, at least about 90%, and/or up to about 100%.

Measures of treatment effect of agitation that may be improved by administering (S)-bupropion (including administering (S)-bupropion to achieve therapeutic plasma levels of one of its metabolites, such as (R,R)-hydroxybupropion) include, but are not limited to, Neuropsychiatric Inventory-Clinician (NPI-C) rating scale, overall and all domains; Neuropsychiatric Inventory-Clinician (NPI-C) rating scale Agitation domain; Cohen-Mansfield Agitation Inventory (CMAI); Cornell Scale for Depression in Dementia (CSDD); Neuropsychiatric Inventory (NPI Agitation/Aggression Domain); Cocomitant Medications (Frequency of using concomitant medications); Alzheimer's Disease Cooperative Study—Activities of Daily Living Inventory (ADC(S)-ADL); Neuropsychiatric Inventory (NPI) Individual Domains and NPI Total Scores (range 0-144), including NPI-C Apathy domain, NPI Agitation/Aggression Caregiver Distress, Modified Alzheimer's Disease Cooperative Study-Clinical Global Impression of Change Agitation (mADC(S)-CGIC Agitation), Patient Global Impression of Change (PGIC) (rated by caregiver), Dementia Quality of Life (DEMQOL), Quality of Life-Alzheimer's disease measure (QoL-AD), Zarit Burden Scale, Resource Utilization in Dementia (RUD), Alzheimer's Disease Assessment Scale-Cognitive Subscale (ADA(S)-Cog), Mini-mental State Examination (MMSE), Caregiver Strain Index (CSI), Individual Domain of the Neuropsychiatric Inventory (NPI), Total Neuropsychiatric Inventory (NPI) Score, Neuropsychiatric Inventory (Agitation/Aggression Domain of NPI), Neuropsychiatric Inventory (Caregiver Distress for NPI Domains), etc.

Substance addiction abuse that may be treated by administering (S)-bupropion (including administering (S)-bupropion to achieve therapeutic plasma levels of one of its metabolites, such as (R,R)-hydroxybupropion) includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, electronic cigarettes, and addiction to chewing tobacco.

Cerebral function disorders that may be treated by administering (S)-bupropion (including administering (S)-bupropion to achieve therapeutic plasma levels of one of its metabolites, such as (R,R)-hydroxybupropion) include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that may be treated by administering (S)-bupropion (including administering (S)-bupropion to achieve therapeutic plasma levels of one of its metabolites, such as (R,R)-hydroxybupropion) include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by administering (S)-bupropion (including administering (S)-bupropion to achieve therapeutic plasma levels of one of its metabolites, such as (R,R)-hydroxybupropion) include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by administering (S)-bupropion (including administering (S)-bupropion to achieve therapeutic plasma levels of one of its metabolites, such as (R,R)-hydroxybupropion) include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated by administering (S)-bupropion (including administering (S)-bupropion to achieve therapeutic plasma levels of one of its metabolites, such as (R,R)-hydroxybupropion) include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by administering (S)-bupropion (including administering (S)-bupropion to achieve therapeutic plasma levels of one of its metabolites, such as (R,R)-hydroxybupropion) include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated administering (S)-bupropion (including administering (S)-bupropion to achieve therapeutic plasma levels of one of its metabolites, such as (R,R)-hydroxybupropion) include, but are not limited to, migraine, tension, and cluster headaches.

Other neurological disorders that may be treated by administering (S)-bupropion (including administering (S)-bupropion to achieve therapeutic plasma levels of one of its metabolites, such as (R,R)-hydroxybupropion) include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, administering (S)-bupropion (including administering (S)-bupropion to achieve therapeutic plasma levels of one of its metabolites, such as (R,R)-hydroxybupropion) may be useful to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), seizures, cough (including chronic cough), etc.

In some embodiments, refractory depression may be treated by administering (S)-bupropion (including administering (S)-bupropion to achieve therapeutic plasma levels of one of its metabolites, such as (R,R)-hydroxybupropion).

(S)-bupropion may also be used (either by direct action of (S)-bupropion, or by administration of (S)-bupropion to achieve therapeutic plasma levels of one of its metabolites, such as (R,R)-hydroxybupropion) to treat, or provide relief to, any type of pain including, but not limited to, musculoskeletal pain, neuropathic pain, cancer-related pain, acute pain, nociceptive pain, inflammatory pain, arthritis pain, complex regional pain syndrome, etc.

In some embodiments, (S)-bupropion may be administered (either for its direct action, or to achieve therapeutic plasma levels of one of its metabolites, such as (R,R)-hydroxybupropion) to relieve neuropathic pain.

Examples of neuropathic pain include diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemo-therapy associated neuropathy, etc.

In some embodiments, (S)-bupropion may be administered (either for its direct action, or to achieve therapeutic plasma levels of one of its metabolites, such as (R,R)-hydroxybupropion) to relieve fibromyalgia.

Adverse events associated with bupropion that may be avoided or reduced by a method described herein include a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and/or tongue protrusion.

Gastrointestinal adverse events include, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

Other adverse events that may be reduced or avoided by a method described herein include abnormal sensation of rotation and movement, agitation, arm weakness, bloating, blurred vision, burning sensation in the eyes, buzzing sound in ear, changes in vital signs (including, but not limited to, heart rate, respiratory rate, body temperature, blood pressure), cold sensation, constipation, difficulty concentrating, difficulty sleeping, difficulty in falling asleep, difficulty urinating, difficulty with bowel movement, discomfort in the ear, discomfort in the eye, discomfort in the stomach, dizziness, dry lips, dry mouth, dry throat, dysmenorrhea, fatigue, feeling feverish, feeling heavy headed, feeling more agitated than usual, feeling more tired than usual, feeling tired, hand tremors, hand weakness, headache, heartburn, hot flashes, increased blood pressure, increased skin sensitivity, increased skin sensitivity at head and face, involuntary muscle contraction, involuntary muscle contractions at all over the body, knee pain, leg weakness, lightheadedness, loose stool, loss of appetite, low back pain, menstrual disorder, metallic taste, more saliva than usual, mucosal dryness, nasal congestion, nausea, runny nose, sensation of light pressure sensation in the eyes, shivers when stretching or yawning, skin sensitivity, skin sensitivity in arm, face, and/or head, sleep difficulties, soft stools, stomach ache, stomach discomfort, sweaty hands and/or feet, throat irritation, throat pain, tinnitus, tremors, and/or weakness. Any of these side effects may also be referred to, or grouped, according to a corresponding, equivalent, or otherwise relevant term found in the Medical Dictionary for Regulatory Activities (MedRA).

The Following Embodiments are Contemplated:

Embodiment 1

A method of providing (R)-bupropion and (S)-bupropion to the plasma, comprising:
  selecting a human being in need of the pharmacokinetic profile provided by orally administering a reference dosage form containing a first amount of racemic bupropion at a first dosing frequency; and orally administering a dosage form containing a second amount of (S)-bupropion that is at least 95% enantiomerically pure at the first dosing frequency to achieve the same pharmacokinetic profile that would be achieved by administering the reference dosage form at the first dosing frequency;

wherein the first dosing frequency is once daily or twice daily; and wherein the second amount is about 40% to about 60% of the first amount.

Embodiment 2

A method of treating a condition that is treatable with racemic bupropion, comprising:

selecting a human patient having the condition that is treatable by orally administering a reference dosage form containing a first amount of racemic bupropion at a first dosing frequency; and orally administering a dosage form containing a second amount of (S)-bupropion that is at least 95% enantiomerically pure at the first dosing frequency to achieve the same therapeutic effect that would be achieved by administering the reference dosage form at the first dosing frequency;

wherein the first dosing frequency is once daily or twice daily; and wherein the second amount is about 40% to about 60% of the first amount.

Embodiment 3

A method of treating a human being comprising orally administering a dosage form containing (S)-bupropion that is at least 95% enantiomerically pure, one or two times per day, to the human being, wherein the human being has a condition that is treatable with (S)-bupropion, wherein the amount of (S)-bupropion administered is selected to be about 20% to about 70% by weight of the amount of racemic bupropion that would be administered to treat the same human being for the same condition.

Embodiment 4

A method of providing therapeutically effective plasma levels of (R,R)-hydroxybupropion comprising orally administering, one or two times per day, a dosage form containing (S)-bupropion that is at least 95% enantiomerically pure, to a human being in need of treatment with (R,R)-hydroxybupropion, wherein (R,R)-hydroxybupropion is at least 97% of the total amount of (R,R)-hydroxybupropion and (S,S)-hydroxybupropion present in the plasma of the human being, and wherein the method achieves a $C_{max}$ of (R,R)-hydroxybupropion that is at least about 500 ng/mL in the human being.

Embodiment 5

A method of treating a human being comprising orally administering a dosage form containing (S)-bupropion that is at least 95% enantiomerically pure to the human being, wherein the human being is in need of treatment with (S)-bupropion, wherein the (S)-bupropion is the sole active agent used to treat the human being.

Embodiment 6

A method of treating a human being comprising orally administering a dosage form containing about 50 mg to about 100 mg of (S)-bupropion that is at least 95% enantiomerically pure, one or two times per day, to the human being, wherein the human being is in need of treatment with (S)-bupropion.

Embodiment 7

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves a $C_{max}$ of (S)-bupropion that is at least about 60 ng/mL.

Embodiment 8

A method of treating a human being comprising orally administering a dosage form containing (S)-bupropion that is at least 95% enantiomerically pure, one or two times per day, to the human being, wherein the human being is in need of treatment with (S)-bupropion, wherein (R,R)-hydroxybupropion is at least 97% of the total of amount of (R,R)-hydroxybupropion and (S,S)-hydroxybupropion present in the plasma of the human being.

Embodiment 9

A method of providing therapeutically effective plasma levels of (R,R)-hydroxybupropion comprising orally administering, one or two times per day, a dosage form containing (S)-bupropion that is at least 95% enantiomerically pure, to a human being in need of treatment with (R,R)-hydroxybupropion, wherein (R,R)-hydroxybupropion is at least 97% of the total of amount of (R,R)-hydroxybupropion and (S,S)-hydroxybupropion present in the plasma of the human being.

Embodiment 10

A method of providing therapeutically effective plasma levels of (R,R)-hydroxybupropion comprising orally administering, one or two times per day, a dosage form containing (S)-bupropion that is at least 95% enantiomerically pure, to a human being in need of treatment with (R,R)-hydroxybupropion, wherein the method achieves a $C_{max}$ of (R,R)-hydroxybupropion that is at least about 500 ng/mL in the human being.

Embodiment 11

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves a $C_{max}$ of (S)-bupropion that is at least about 70 ng/mL.

Embodiment 12

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves an $AUC_{0-12}$ of (S)-bupropion that is at least about 600 ng·h/mL.

Embodiment 13

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves a $C_{max}$ of (R,R)-hydroxybupropion that is at least about 800 ng/mL.

Embodiment 14

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves an $AUC_{0-12}$ of (R,R)-hydroxybupropion that is at least about 8,000 ng·h/mL.

Embodiment 15

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves a $C_{max}$ of erythrohydroxybupropion that is at least about 90 ng/mL.

Embodiment 16

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves an $AUC_{0-12}$ of erythrohydroxybupropion that is at least about 1,000 ng·h/mL.

Embodiment 17

A method of treating a human being comprising orally administering a dosage form containing (S)-bupropion that is at least 95% enantiomerically pure, one or two times per day, to the human being, wherein the human being is in need of treatment with (S)-bupropion, wherein the method achieves a $C_{max}$ of threohydroxybupropion that is at least about 450 ng/mL.

Embodiment 18

A method of treating a human being comprising orally administering a dosage form containing (S)-bupropion that is at least 95% enantiomerically pure, one or two times per day, to the human being in need of treatment with (S)-bupropion, wherein the method achieves an $AUC_{0-12}$ of threohydroxybupropion that is at least about 5,000 ng·h/mL.

Embodiment 19

The method of embodiment 1, 2, 3, 4, 5, 6, 7, 8, 9, 10, 11, 12, 13, 14, 15, 16, 17, or 18, wherein the human being is in need of treatment with (S)-bupropion.

Embodiment 20

The method of embodiment 1, 2, 3, 4, 5, 6, 7, 8, 9, 10, 11, 12, 13, 14, 15, 16, 17, 18, or 19, wherein the method achieves a $C_{max}$ of (S)-bupropion that is at least about 60 ng/mL.

Embodiment 21

The method of embodiment 1, 2, 3, 4, 5, 6, 7, 8, 9, 10, 11, 12, 13, 14, 15, 16, 17, 18, 19, or 20, wherein the method is effective in increasing the $C_{max}$ of (S)-bupropion at least 5-fold as compared to the $C_{max}$ of (R)-bupropion that results from administering the same amount of (R)-bupropion to the human being.

Embodiment 22

The method of embodiment 1, 2, 3, 4, 5, 6, 7, 8, 9, 10, 11, 12, 13, 14, 15, 16, 17, 18, 19, 20, or 21, wherein the method achieves a $C_{max}$ of (R,R)-hydroxybupropion that is at least about 500 ng/mL in the human being.

Embodiment 23

The method of embodiment 1, 2, 3, 4, 5, 6, 7, 8, 9, 10, 11, 12, 13, 14, 15, 16, 17, 18, 19, 20, 21, or 22, wherein the method is effective in increasing the $C_{min}$ of (R,R)-hydroxybupropion at least 3-fold as compared to the $C_{min}$ of (R,R)-hydroxybupropion that results from administering the same amount of (R)-bupropion to the human being.

Embodiment 24

The method of embodiment 1, 2, 3, 4, 5, 6, 7, 8, 9, 10, 11, 12, 13, 14, 15, 16, 17, 18, 19, 20, 21, 22, or 23, wherein the dosage form is administered once daily.

Embodiment 25

The method of embodiment 1, 2, 3, 4, 5, 6, 7, 8, 9, 10, 11, 12, 13, 14, 15, 16, 17, 18, 19, 20, 21, 22, 23, or 24, wherein the dosage form is administered twice daily.

Embodiment 26

The method of embodiment 1, 2, 3, 4, 5, 6, 7, 8, 9, 10, 11, 12, 13, 14, 15, 16, 17, 18, 19, 20, 21, 22, 23, 24, or 25, wherein (R,R)-hydroxybupropion is at least 97% of the total of amount of (R,R)-hydroxybupropion and (S,S)-hydroxybupropion present in the plasma of the human being.

Embodiment 27

The method of embodiment 1, 2, 3, 4, 5, 6, 7, 8, 9, 10, 11, 12, 13, 14, 15, 16, 17, 18, 19, 20, 21, 22, 23, 24, 25, or 26, which is effective in providing therapeutically effective plasma levels of (R,R)-hydroxybupropion.

Embodiment 28

The method of embodiment 1, 2, 3, 4, 5, 6, 7, 8, 9, 10, 11, 12, 13, 14, 15, 16, 17, 18, 19, 20, 21, 22, 23, 24, 25, 26, or 27, which is effective in providing therapeutically effective plasma levels of (S)-bupropion.

Embodiment 29

The method of embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein the human being is in need of treatment with (R,R)-hydroxybupropion.

Embodiment 30

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, or 29, wherein the method achieves a $C_{max}$ of (R,R)-hydroxybupropion that is at least about 500 ng/mL in the human being.

Embodiment 31

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the dosage form is administered for at least 8 consecutive days.

Embodiment 32

The method of embodiment 31, wherein the dosage form is administered for at least 14 consecutive days.

Embodiment 33

The method of embodiment 31, wherein the dosage form is administered for at least 21 consecutive days.

Embodiment 34

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, wherein the dosage form contains about 60 mg to about 90 mg of (S)-bupropion.

Embodiment 35

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34, wherein the dosage form is administered once daily for 1 to 3 consecutive days, then the dosage form is administered twice a day for at least the following 4 to 7 consecutive days, so that the dosage form is administered once daily or twice daily for a total of at least 8 consecutive days.

Embodiment 36

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, wherein the dosage form is administered once daily for 1 to 7 consecutive days, then the dosage form is administered twice a day for at least the following 7 consecutive days, so that the dosage form is administered once daily or twice daily for a total of at least 8 consecutive days.

Embodiment 37

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, wherein the dosage form contains about 70 mg to about 80 mg of the (S)-bupropion.

Embodiment 38

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37, wherein the method achieves a $C_{max}$ of (S)-bupropion in the human being that is at least about 70 ng/mL.

Embodiment 39

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38, wherein the method achieves an $AUC_{0-12}$ of (S)-bupropion in the human being that is at least about 400 ng·hr/mL.

Embodiment 40

The method of embodiment 39, wherein the method achieves an $AUC_{0-12}$ of (S)-bupropion in the human being that is about 500 ng·hr/mL to about 900 ng·hr/mL.

Embodiment 41

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, wherein the dosage form provides sustained release of the (S)-bupropion.

Embodiment 42

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41, wherein the dosage form contains about 70 mg to about 80 mg of the (S)-bupropion.

Embodiment 43

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42, wherein the method achieves a $C_{max}$ of (R,R)-hydroxybupropion in the human being that is at least about 600 ng/mL.

Embodiment 44

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, wherein the method achieves an $AUC_{0-12}$ of (R,R)-hydroxybupropion in the human being that is at least about 7000 ng·hr/mL.

Embodiment 45

The method of embodiment 44, wherein the method achieves an $AUC_{0-12}$ of (R,R)-hydroxybupropion in the human being that is at least about 8000 ng·hr/mL.

Unless otherwise indicated, all numbers expressing quantities of ingredients, properties such as amounts, AUC values, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A method of treating attention deficit/hyperactivity disorder (AD/HD) comprising administering an (S)-bupropion to a human being in need thereof, wherein the (S)-bupropion is administered at a daily dose that is therapeutically effective for treating AD/HD and is about 1 mg to about 150 mg of at least 95% enantiomerically pure (S)-bupropion.

2. The method of claim 1, wherein the human being has an age of about 18 years or less.

3. The method of claim 1, wherein the (S)-bupropion is administered in a dosage form containing a binder.

4. The method of claim 1, wherein the (S)-bupropion is administered in a dosage form containing an excipient.

5. The method of claim 1, wherein the (S)-bupropion is administered in a dosage form containing a disintegrating agent.

6. The method of claim 1, wherein the (S)-bupropion is administered in a dosage form containing a lubricant.

7. The method of claim 1, wherein the method achieves a $C_{max}$ of (S)-bupropion in the human being that is at least about 60 ng/mL.

8. The method of claim 1, wherein the method is effective in achieving a $C_{max}$ of (S)-bupropion that is at least 5-fold greater than the $C_{max}$ of (R)-bupropion that results from administering the same amount of (R)-bupropion to the human being.

9. The method of claim 1, wherein the method achieves a $C_{max}$ of (R,R)-hydroxybupropion that is at least about 500 ng/mL in the human being.

10. The method of claim 1, wherein the method is effective in achieving a $C_{min}$ of (R,R)-hydroxybupropion that is at least 3-fold greater than the $C_{min}$ of (R,R)-hydroxybupropion that results from administering the same amount of (R)-bupropion to the human being.

11. The method of claim 1, wherein administering the (S)-bupropion results in (R,R)-hydroxybupropion that is at least 97% of the total amount of hydroxybupropion present in the plasma of the human being.

12. The method of claim 1, wherein the (S)-bupropion is administered for at least 8 consecutive days.

13. The method of claim 1, wherein the (S)-bupropion is administered for at least 14 consecutive days.

14. The method of claim 1, wherein the (S)-bupropion is administered for at least 21 consecutive days.

15. The method of claim 1, wherein the method achieves an $AUC_{0-12}$ of (S)-bupropion in the human being that is at least about 400 ng·hr/mL.

16. The method of claim 1, wherein the method achieves an $AUC_{0-12}$ of (S)-bupropion in the human being that is about 500 ng·hr/mL to about 900 ng·hr/mL.

17. The method of claim 1, wherein the (S)-bupropion is orally administered in a dosage form that provides sustained release of the (S)-bupropion.

18. The method of claim 1, wherein the method achieves a $C_{max}$ of (R,R)-hydroxybupropion in the human being that is at least about 600 ng/mL.

19. The method of claim 1, wherein the method achieves an $AUC_{0-12}$ of (R,R)-hydroxybupropion in the human being that is at least about 7000 ng·hr/mL.

* * * * *